(12) United States Patent
Ziemeck et al.

(10) Patent No.: US 9,233,026 B2
(45) Date of Patent: Jan. 12, 2016

(54) VISION AID WITH THREE-DIMENSIONAL IMAGE ACQUISITION

(71) Applicant: IMI INTELLIGENT MEDICAL IMPLANTS AG, Zug (CH)

(72) Inventors: Patrick Ziemeck, Gera (DE); Marcus Dapper, Bonn (DE); Christian Kopka, Bonn (DE); Ralf Hornig, Bonn (DE)

(73) Assignee: PIXIUM VISION SA, Paris (FR)

( * ) Notice: Subject to any disclaimer, the term of this patent is extended or adjusted under 35 U.S.C. 154(b) by 22 days.

(21) Appl. No.: 13/931,101

(22) Filed: Jun. 28, 2013

(65) Prior Publication Data
US 2014/0009591 A1 Jan. 9, 2014

Related U.S. Application Data

(63) Continuation of application No. 12/519,358, filed as application No. PCT/EP2007/011133 on Dec. 18, 2007, now Pat. No. 8,503,713.

(30) Foreign Application Priority Data

Dec. 19, 2006 (DE) .......................... 10 2006 060 045

(51) Int. Cl.
*G06K 9/00* (2006.01)
*A61F 9/08* (2006.01)
(Continued)

(52) U.S. Cl.
CPC .............. *A61F 9/08* (2013.01); *A61N 1/36046* (2013.01); *G02B 27/017* (2013.01); *G02B 2027/014* (2013.01); *G02B 2027/0132* (2013.01); *G02B 2027/0138* (2013.01)

(58) Field of Classification Search
None
See application file for complete search history.

(56) References Cited

U.S. PATENT DOCUMENTS

| 5,106,179 A | 4/1992 | Kamaya et al. |
| 6,400,989 B1 | 6/2002 | Eckmiller |

(Continued)

FOREIGN PATENT DOCUMENTS

| EP | 1666088 | 6/2006 |
| JP | 2001-204757 | 7/2001 |

(Continued)

OTHER PUBLICATIONS

PCT International Search Report relating to International Application No. PCT/EP2007/011133, date of mailing of Search Report Aug. 4, 2008 (3 pgs. in German, 3 pgs. in English).

(Continued)

*Primary Examiner* — Atiba O Fitzpatrick
(74) *Attorney, Agent, or Firm* — Workman Nydegger

(57) ABSTRACT

The task of providing a device which makes it possible for the natural visual faculty of a partially vision-impaired person to be restored or supported as realistically as possible by means of a visual aid or visual prosthesis is achieved with the visual aid according to the invention in that, beyond the pure acquisition of a two-dimensional image, additional information is included in the image processing. For this purpose, a visual aid system is proposed which, during the reproduction of the processed image, visualizes additional information regarding the spatial position and/or specific attributes of objects in the acquired image which is associated with objects in the acquired image. The present invention thus affords the advantage that a three-dimensional image of the current environment of the user can be acquired owing to the fact that the image visualized to the user by the visual aid system according to the invention comprises additional information, for example, about the relative distance of the objects contained in the image and a depth-selective representation of the acquired image can thus be achieved.

7 Claims, 5 Drawing Sheets

(51) Int. Cl.
*A61N 1/36* (2006.01)
*G02B 27/01* (2006.01)

(56) References Cited

U.S. PATENT DOCUMENTS

| | | |
|---|---|---|
| 2002/0101568 A1 | 8/2002 | Eberl et al. |
| 2004/0117011 A1 | 6/2004 | Aharoni et al. |
| 2004/0236389 A1 | 11/2004 | Fink et al. |
| 2005/0021282 A1 | 1/2005 | Sammut et al. |
| 2010/0220176 A1 | 9/2010 | Ziemeck et al. |

FOREIGN PATENT DOCUMENTS

| | | |
|---|---|---|
| JP | 2001204757 | 7/2001 |
| WO | WO97/17043 | 5/1997 |
| WO | WO98/36795 | 8/1998 |
| WO | WO2004/054469 | 7/2004 |
| WO | WO2004/087024 | 10/2004 |

OTHER PUBLICATIONS

Office Action U.S. Appl. No. 12/519,358, filed Aug. 3, 2012.
Office Action U.S. Appl. No. 12/519,358, filed Nov. 19, 2012.
Notice of Allowance U.S. Appl. No. 12/519,358, filed Mar. 28, 2013.

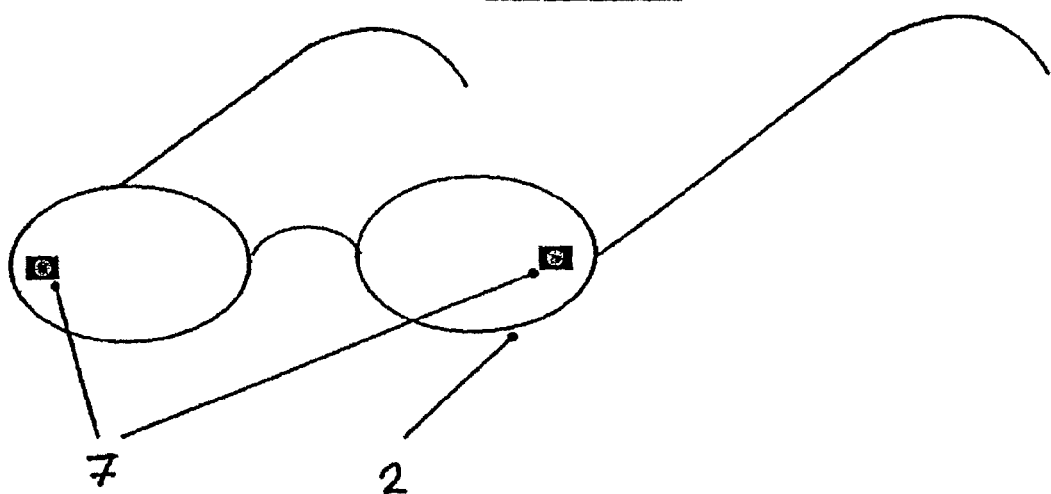
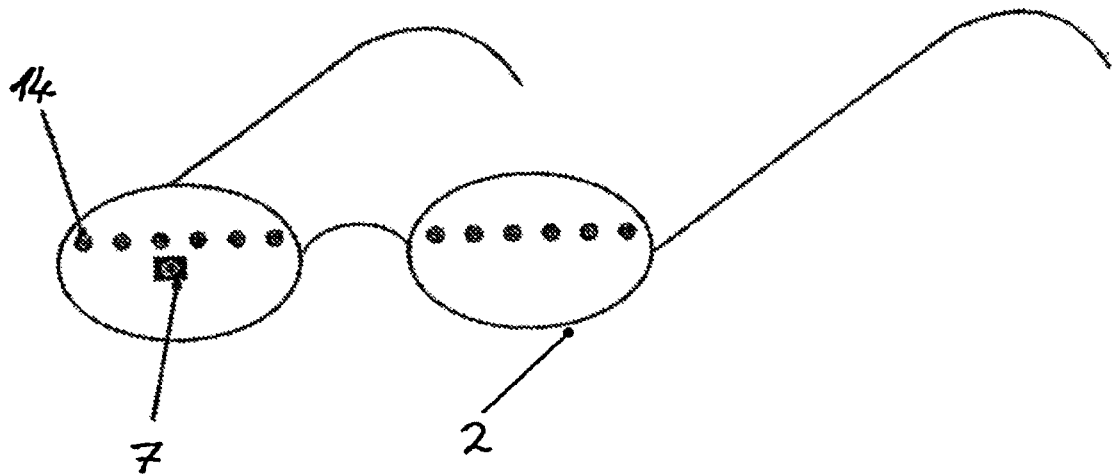

VISION AID WITH THREE-DIMENSIONAL IMAGE ACQUISITION

CROSS-REFERENCE TO RELATED APPLICATIONS

This application is a continuation of U.S. patent application Ser. No. 12/519,358 having a filing date of 15 Jun. 2009 and having a 371(c) date of 23 Mar. 2010, which is a U.S. National Stage of International Application No. PCT/EP2007/011133 having an international filing date of 18 Dec. 2007, which claims priority to German Patent Application No. 10 2006 060 045.2, filed on 19 Dec. 2006, each of the foregoing applications are hereby incorporated by reference in their entirety.

BACKGROUND

The present invention relates to a vision aid with three-dimensional image and information acquisition. A vision aid in the sense of the present invention also encompasses other image acquisition systems, such as e.g. residual-light amplifier or night vision apparatus for assisting the human visual faculty. Such vision aids or visual prostheses, such as e.g. a retina implant, can also encompass functions for image enlargement or for residual-light amplification.

Vision aids have already been developed in the form of implants for the retina of the human eye, which are provided for the treatment of patients, whose visual faculty has been partially or completely lost through defects in the retina. In the process, a microelectronic device is implanted in the region of the retina with a plurality of light-sensitive pixel elements, on which an image projected onto the retina via the still-intact natural light path of the eye is received. In other visual prostheses, the image acquisition occurs through an external camera, in particular a video camera, which is preferably accommodated in spectacles. The image acquired through the pixel elements or the camera is converted into electrical signals and delivered via stimulation electrodes by means of electrical stimulation impulses to the ganglion cells of the retina and the optic nerve, thereby to restore or to improve the visual faculty of the patient. The known vision aids have the disadvantage, however, that they exclusively process the image acquired via the natural light path of the eye or from the external camera. The thereby resulting image is therefore merely two-dimensional and contains no three-dimensional information.

In order to restore or to assist the natural visual faculty by means of a vision aid or a visual prosthesis as realistically as possible, it is therefore desirable to incorporate additional information in the image processing beyond the pure acquisition of a two-dimensional image.

This task is solved by the inventive device having the features according to claim 1. Preferred embodiments of the present invention are characterized in the sub-claims.

SUMMARY

The present invention solves the above-mentioned task by a vision aid system with at least one camera for acquisition of an image having a plurality of image data, electronic means for processing the acquired image data, and a stimulation device implantable in the body at the visual organ for reproduction of the processed image via corresponding stimulation of the visual organ, wherein, in the reproduction of the processed image, additional information and/or particular attributes regarding the spatial position of objects in the acquired image are visualized, these being associated with objects in the acquired image.

With a vision aid according to the present invention, objects in the immediate vicinity of the user can in particular be specially visualised or accentuated, while more distant objects can optionally be masked out. The accentuation of particular objects can also occur through the use of different grey-scales or varying colours. In this way, objects located in the near vicinity may, for example, be represented in another colour or grey-scale than more distantly lying objects. The present invention thus offers the advantage that a three-dimensional copy of the current environment of the user can be acquired, in which the image visualized by the user from the vision aid system according to the invention comprises additional information, for example, about the relative distance of the objects contained in the image and may thereby achieve a depth-selective representation of the acquired image.

The advantage of the depth-selective representation resides in that the user of the vision aid system can receive a visually well-structured and easily interpreted visual impression of the near or more distant vicinity despite a limited pixel resolution, colour graduation, grey shading or limited member of picture elements (pixels) of the vision aid system. The vicinity of the user can then, for example, be visualised via an outline representation, which is able to be realised with a relatively low number of simultaneously activated picture elements.

According to the present invention, the entire system of the vision aid comprises spectacles and optionally an additional unit carried on the body, e.g. a pocket computer, which can be carried at any desired position of the body and can communicate and exchange image data with the spectacles via a cable connection or alternatively via wireless radio connection. In a special application of the present invention to an above-described retina implant system, a device implanted in the body can additionally be provided, which receives the image data acquired by the external camera.

In a preferred embodiment of the present invention, a three-dimensional map for preparation of the depicted image section is employed. A three-dimensional map of the vicinity of a particular image section is able to be employed in the form that only the segments of the image are depicted that are present in the near or middle distance of the user of the vision aid, because these may be of greater interest for the user than segments of the image or objects, which are located at a greater distance. Alternatively, in a special operating mode of the vision aid according to the invention, only more distant objects may be depicted, in the event the user of the vision aid preferably wants to visualise the background of the acquired image or the more distant objects.

The different operating modes of the vision aid can either be rigidly implemented in the image processing of the system or be available optionally selectable for the user. The selection of the operating modes can be effected via activation elements of the spectacles, via the optionally provided pocket-computer, or via a remote control, which may be worn at any desired position on the body.

The display area of the system is able to be set through correspondingly selected mathematical intersection surfaces or surface functions in a three-dimensional model of the pocket computer. As intersection surfaces, sections of planar surfaces or a cylindrical or a spherically surface or other desirably formed intersection surfaces may, for example, be selected. According to the operating mode of the implant system, only the intersection surfaces with the acquired objects are thereby depicted in the three-dimensional model of the pocket computer (or the spectacles).

Through a setting device of the implant system, the user of the vision aid can select such an operating mode, for example, a scan mode, with which only those objects are depicted that are located in a particular acquisition area of the system. Further, the user of the vision aid can vary the optical acquisition area of the system by means of the setting device. In a particular operating mode of the system according to the invention, the optical acquisition area of the system can be repeatedly expanded and then contracted again, so that the user of the vision aid continuously receives spatial section images of the environment presented.

According to a further preferred embodiment, the vision aid according to the invention can, by means of the electronic calculating capacity of the pocket computer with the acquired image data, generate a three-dimensional map and visualize this to the user. With a three-dimensional map, an image section can also be presented to the user of the vision aid, for example, in a birds-eye perspective, in which an outline of the current environment and the objects located therein is depicted, which can be especially helpful for navigation in an unclear environment.

These operating modes may not only be employed with vision aids for users having extremely reduced visual capacity, but also in visualization systems for orientation systems for users with normal visual capacity. The present invention can also be applied in vision aids in which a video camera integrated in the spectacles acquires the image and is projected onto the retina of a vision impaired user via a display also integrated in the spectacles. In the process, even coarse pixel presentations may achieve an improvement of the visual impression.

In a further preferred embodiment of the vision aid according to the invention, a three-dimensional map is generated by use of only one camera. In the process, the camera which is integrated in the spectacles of the user for acquisition of the image information is preferably used, in order to carry out a stereoscopic image processing. In this connection, images from different spatial positions of the camera can be used, which have been recorded after one another with slight time offset. For this purpose, the relative spatial positions and the relative angular orientations of the camera must be taken into account, which will be explained in the following section.

The spectacles, in which the camera is integrated, may for example be equipped with three-dimensional acceleration sensors, which respectively ascertain the acceleration $[\ddot{x}\ \ddot{y}\ \ddot{z}]$ of the spectacles and thereby the acceleration of the camera in the three spatial directions $[x, y, z]$. Alternatively, the spectacles in which the camera is integrated may be equipped with a six-dimensional acceleration sensor, which respectively ascertains the acceleration of the spectacles and thereby the acceleration of the camera in the three spatial directions $[x, y, z]$ as well as the angular acceleration $[\ddot{x}\ \ddot{y}\ \ddot{z}\ \ddot{\phi}_x\ \ddot{\phi}_y\ \ddot{\phi}_z]$ of the reference system of the spectacles about the three spatial axes. The dimensionality of a sensor consequently specifies the number of the measured variables that a sensor may ascertain. A six-dimensional acceleration sensor ascertains, for example, three translational accelerations and three angular accelerations, which have an orthogonal reference to one another and thereby ascertains a total of 6 orthogonal acceleration measurements.

In order to determine the current camera position relative to a previous camera position, an inertial navigation method may be used. For this purpose, one, two or more acceleration sensors (one-dimensional, two-dimensional, three-dimensional or multi-dimensional, e.g. six-dimensional acceleration sensors can be placed at kinematically well-conditioned positions in the spectacles. Kinematically well-conditioned positions are, for example, such positions that are sufficiently well spaced from one another within the spectacles.

Through double integration of the above-mentioned six orthogonal acceleration measurements, the relative position $[\Delta x\ \Delta y\ \Delta z\ \Delta \phi_x\ \Delta \phi_y\ \Delta \phi_z]$ of the spectacles or the camera position can be determined relative to a previous camera position. The integration of the acceleration measurements and the calculation of the position and orientation of the spectacles occurs advantageously through electronic integrators in a calculator unit integrated in the vision aid system, which is accommodated either in the spectacles or outside of the spectacles, e.g. in a unit ("pocket computer") carried on the body of the user, or can be distributed onto the spectacles and the unit carried on the body. In so doing, the unit carried on the body can communicate with the spectacles either per cable connection and/or via wireless connection (e.g. by means of Bluetooth, WLAN or other communication technology).

The time integration increment in the integration of the acceleration measurements should be sufficiently smaller than the time span within which the acceleration of the spectacles changes substantially, in order to be able to measure sufficiently precise changes in position of the spectacles or camera over a limited time period, e.g. 10 seconds, with which then at least two or more camera images can be acquired from different positions of the camera.

By means of the above-mentioned double integration, a six-dimensional relative position vector is generated from the six orthogonal acceleration measurements of a 6D-acceleration vector, which specifies the difference of a previous position of the camera to a subsequent camera position. This six-dimensional relative position vector contains three location differential coordinates ($\Delta x$, $\Delta y$, $\Delta z$), which specify the deviation of the location coordinates (x, y, z) of the previous camera position to the subsequent camera position, and three angular differential coordinates ($\Delta \phi x$, $\Delta \phi y$, $\Delta \phi z$), which specify the deviation of the angular position ($\phi x$, $\phi y$, $\phi z$) of the previous camera position to the subsequent camera position. The integration can be effected in discrete time increments or can be carried out continuously.

In this way, a sequence of camera images at respectively different camera positions can be acquired, wherein a sequence consists of at least two camera images. A relative position in reference to the previous or the subsequent camera image is assigned to each camera image of this sequence, for example, by means of the above-mentioned location differential coordinates and angular differential coordinates. Camera images can also be recorded in fixed time intervals with correlated position, wherein older images can optionally be increasingly more weakly weighted in the influence on the current spatial calculation until they ultimately have no further influence. In this way, the effect that the position determination by means of the inertial navigation over greater time spans can include increasing inaccuracies in the form of a position drift is counteracted.

In a further preferred embodiment of the vision aid according to the present invention, an assignment of camera images and camera positions to different measurement time points can be undertaken. Thus, a second camera, which would otherwise be needed for taking stereo images, can be advantageously saved without dispensing with three-dimensional images. Further, more than two images from different positions and orientations can be processed, in order to thereby generate a more complete three-dimensional map of the environment of the user of the vision aid, which may take place e.g. by means of the known "batch compensation method". A prerequisite for this method are small head movements of the user in the order of magnitude of the eye separation of two human eyes. The camera may then respectively acquire one image from different positions and thereby deliver the two images to the calculator unit in short time succession, which a human with normal visual capacity would acquire with both eyes. The calculator unit can thereupon separately prepare the two camera images and update and expand the three-dimensional model in the pocket computer.

Furthermore, at the beginning of the above mentioned integration, a measurement of the speed-offsets can be carried out in order to improve the measurement accuracy and thus the allocation of the acquired camera images to the calculated local- and angular-positions of the camera. This can occur in different possibilities:

The user of the vision aid may, through corresponding input means, set the speed of the spectacles to zero, e.g. upon keeping the spectacles still for a short time period. This can, for example, also occur through brief placement of the spectacles onto a motionless support. With sufficiently high accuracy of the acceleration sensors and the electronic integrators, it can also suffice to reference the spectacles with the speed-offset zero during the charging process, where they are with high probability at rest, and to start the integration from this time point and to employ this speed-offset for the entire daily use.

The current absolute speed can also be determined with the aid of other navigation resources, for example, by means of GPS or similar radio triangulation methods. Further, the current speed of the spectacles or the user of the vision aid can be ascertained via the change of the image information in combination with the acceleration measurement data of the spectacles. In addition to the above-mentioned speed determination, the possibility also exists to determine the current position of the spectacles of the user by means of GPS or similar radio triangulation methods. The orientation of the spectacles in space, i.e. the angular positions of the spectacles, can be ascertained through evaluation of the previous angular position values or e.g. with a compass (e.g. a Hall probe) or through similar orientation measurement methods. The angle about the nodding axis of the spectacles (inclination angle), which is not ascertainable with a compass, may for example be ascertained via a gravitation-based inclination sensor.

A combination of the above-mentioned methods can also be employed, in order to minimize the measurement error of the sensors integrated in the spectacles, particularly in order to specifically treat exceptions that can arise with the different methods. This applies in particular in event that parts of the environment of the user move quickly or the user is located in a fast-moving inertial system, like e.g. a train, car, or aircraft.

According to a further preferred embodiment of the vision aid according to the invention, the preparation of stereoscopic or three-dimensional information with respect to the spatial environment in the visual field of the user occurs through the use of a second camera in the spectacles. In the process, the second camera is preferably also integrated in the spectacles and spaced as far as possible from the first camera in the spectacles. Because of the known, fixed separation of the two cameras from one another, stereoscopic depth information about segments of the current image section is able to be calculated from the two slightly different images, which can then be converted by the electronic calculator unit to a three-dimensional map of the environment of the user and conveyed to the user via stimulation means.

In a still further preferred embodiment of the vision aid according to the invention, distance sensors are alternatively or additionally employed, such as e.g. ultrasound sensors, rotating laser scanners in the visible or invisible wavelength range, e.g. in the ultraviolet or infrared light range. With the aid of such distance sensors, the environment of the implant-wearer can be better captured and thereby obstacles also better identified. The information acquired from the distance sensors can, for example, be further processed with triangulation methods and assigned to corresponding sections of the acquired camera image or the camera image sequences. In this respect, multiple sensors may e.g. be arranged in the form of a one-dimensional or multi-dimensional array. In this preferred embodiment of the present invention, the spectacles comprise one- or multi-dimensional arrays of sensors or actuators, such as e.g. ultrasound sensors, infrared sensors, photo-sensors, lasers or other sensors or actuators or combinations thereof.

In a further preferred embodiment of the vision aid according to the invention, a stripe projection or structured illumination is carried out. In the process, a homogenous or a structured (e.g. "gray coded") stripe-pattern is projected onto the environment of the user, preferably with infrared light, e.g. with laser light. The generation of a stripe pattern occurs, for example, through a projection template, which is positioned in front of a light beam. In this connection, interference effects can alternatively e.g. with use of a laser beam be advantageously used in order to generate a corresponding pattern in the environment of the user. Alternatively, for example, a light beam can be diverted with the aid of a micro-mirror system and parallel time-modulated to capture the current visual field of the user.

The stripe pattern is invisible with the use of infrared light. The camera in the spectacles of the vision aid is, however, sensitive to infrared light and can detect the stripe pattern. Distortions of this stripe pattern (e.g. deflections, displacements) can be transformed back through corresponding triangulation methods into dimensional depth information, through which a three-dimensional map of the current image section is, in turn, able to be calculated.

In this connection, the stripe pattern may also be periodically activated in defined time sections which lie between the time points at which the original video image is recorded (e.g. 10 ms stripe pattern, 490 ms no stripe pattern). The actual image of the environment is hereby also simultaneously available, which can, for example, be applied for a so-called "texture mapping" of the current environment onto the currently depicted object. Instead of a "texture mapping", the currently not-displayed objects can also be masked out with the three-dimensional map, so that only the image sections of the currently depicted objects are visible, which is accomplishable with relatively low computing effort. In this way, the environment of the user of the vision aid can be depicted more clearly.

In a further preferred embodiment of the vision aid according to the invention, the spectacles are equipped with a camera and a grid projector, such as e.g. a laser projector with deflection unit, with a projection mask having a light source or other projection means. In this embodiment, the sampling of the visual field detected by the vision aid system occurs by means of a laser beam, which is positioned with a corresponding deflection unit in the beam path of the laser, such as e.g. a piezo-technology driven micro-mirror system or rotating mirror system. The camera image can thereby be used for position determination of the picture element, from which the position of the reflecting object segment is then, e.g. through triangulation, again able to be ascertained. Alternatively, a fast XY-photo-detector can also be employed, which can ascertain the current position of the picture element in the environment of the user and thereby make possible a sampling of the entire user environment in the range of seconds.

In a further preferred embodiment of the vision aid according to the invention, a time duration measurement of the reflected laser light is undertaken with the aid of a fast photo-detector. The time duration between the moment of transmission of the respective laser light impulse and the moment of reception of the reflected laser light impulse in the photo-detector is hereby ascertained and, taking account of the speed of light, the distance of the related picture element is calculated there-from. Afterwards, a three-dimensional map of the related image section is able to be constructed through evaluation of the measurements for the image raster.

According to a further preferred embodiment of the present invention, the three-dimensional map generated by the pocket computer can also be filed in an external three-dimensional data storage, wherein particular objects, critical terrain shapes or important items in the image area acquired by the vision aid system can be specially characterized or accentuated. That way, the following particular objects of an everyday environment can, for example, be particularly characterized in the three-dimensional map of the vision aid system: staircase steps, light-posts, traffic lights, zebra crossings, curb-stone edges, ground unevenness, motor vehicles, bicycles or other vehicles of different types and shapes, people, faces, body parts, door frames, window frames, tables, crockery or other important objects, which require the particular attention of the observer or the user of the vision aid system.

The particular objects are preferably automatically detected by comparison with an image library stored in the pocket computer or in the external data storage. This image library may be filled with any desired image samples that could be of importance to the user of the vision aid system, such as e.g. pictures of a traffic light or of other important objects from various viewing directions. Through permanent comparison of the video images acquired or recorded by the vision aid system with the image samples saved in the image library, these particular objects in the video image can be automatically recognized and thereafter characterized in the three-dimensional map.

The acquisition of image components in the three-dimensional map generated by the pocket computer can, for example, take place through the known Gabor filtering or other methods of image segmentation. For this purpose, for example, each picture element vector $Pi=(xi, yi, zi)$ of the three-dimensional map can be provided with a characteristic variable $Ei$, from which an expanded picture element vector $Pi=(xi, yi, zi, Ei)$ with $(i=1, \ldots, N)$ results. This characteristic variable $Ei$ may represent either simple attributes in binary manner, such as e.g. important or unimportant, or also an grading in different classes, such as e.g. not interesting, interesting, very interesting, helpful or dangerous. Objects with one of these attributes or characteristics can then be visualized in the image section depicted by the vision aid system by means of special effects, e.g. by flashing, a representation with greater brightness, by special coloration or other markings.

According to a further preferred embodiment of the vision aid system according to the invention, the distance measurement of picture elements or objects in the environment of the user occurs with the aid of a laser distance sensor. Such a laser distance sensor typically comprises a laser beam rotating around the z-spatial axis, which can sample the environment line-by-line with each revolution, wherein, depending upon the mounting position, a sampling of up to a complete angular circumference of 360° is possible. The laser beam source is positioned on a rotating platform, which for its part may acquire the current rotational angle z of the platform (0° to 360°).

The laser source of a laser distance sensor transmits laser light impulses in time intervals sufficiently far spaced from one another, which impulses are reflected from objects in the scanned environment and whose return at the location of their transmission is time-measured by means of a photo-detector. The capture of the emitted and reflected light impulse is, for example, carried out with the aid of a photodiode and the time duration of the light impulse ascertained with sufficiently fast electronics. From the measured time interval (duration t) between the emission of the laser impulse and the return of the laser impulse and the speed of light (c=3 108 m/s), the distance s of the object struck by the laser pulse is able to be calculated from the product according to the formula $s=\frac{1}{2} v t$. An advantage of the distance measurements by means of a laser distance sensor resides in that, a very small picture element can be projected by the laser beam onto the environment, such that a detailed scanning and resolution of the object surface is able to be obtained.

In order to obtain a complete image of the environment and to acquire the entire image surface, it is necessary to sample more than one image line. For this purpose, the laser beam of the laser distance sensor must be additionally deflected in the vertical direction, in order to sample the image columns in a desired angular section. This can, for example, take place with a mirror pivotable about the x-axis, which is similarly equipped with an angle measuring device for the angle x about the x-spatial axis. With the angles x, z and the distance s, the position $PS=(xS, yS, zS)$ of the sighted picture element is able to be calculated directly via triangulation and to be adopted as spatial point in the three-dimensional map generated by the vision aid system.

As laser source, a so-called VCSEL (Vertical Cavity Surface Emitting Laser) is, for example, able to be used. Such a component exhibits a small edge length of about 300 μm and is therefore well able to be integrated in the spectacles of the vision aid system. As vertical deflection unit, a commercially available micro-mirror can, for example, be used, such as that already employed e.g. in video-projectors. The rotation of the micro-mirror about the z-spatial axis may, for example, occur with a rotating, mirrored prism, which is driven by a micro-motor. Dimensions for the entire assembly can thus be achieved below 10 mm edge length, which can be accommodated in the spectacles of the vision aid system. If a VCSEL is used with infrared laser light outside of the visible spectral range, the sampling of the environment can thus occur without persons in the vicinity of the user being disturbed or taking notice.

As described above, the three-dimensional information acquisition and further processing of the acquired image data of the vision aid system can be supported by an externally generated three-dimensional map of the acquired image data. The three-dimensional map is preferably generated by means of the electronic components of the pocket computer and stored on the pocket computer or on an external three-dimensional data storage, such as e.g. an electronic server, in wireless connection with the vision aid system (e.g. via WLAN or Bluetooth).

The three-dimensional map can also be made available as electronic map material via external sources, for example, through a map for navigation systems which are transferred to the server or the pocket computer via a CD or other storage medium or per Internet connection. With such electronic map material, the environment is, as a general rule, pictured in the form of grid networks onto which an image of the world surface recorded by video can optionally be wrapped or projected.

With the three-dimensional map, it can also concern three-dimensional information specially produced or prepared for a retina implant system which contains a detailed profile of the near vicinity. The adequate minimal resolution of such a depiction preferably lies in the order of magnitude from a few millimeters to centimeters. The three-dimensional map can, for example, contain N individual grid points $Pi=(xi, yi, zi)$ with ($i=1, \ldots, N$), which correspond with particular pixels or surface points of the related environment. These grid points can be connected with neighbouring points by lines in order to thereby span a grid network.

An electronically recorded image, for example, in the form of a photograph of the environment, can be wrapped or projected onto the surfaces spanned in this grid network in the three-dimensional map. This occurs advantageously with the known method of so-called "texture mapping", with which a three-dimensional picture of the environment is generated. With the position $PB=(xB, yB, zB)$ and orientation $B=(Bx, By, Bz)$ of the observer or of the spectacles of the user of the vision aid system, the currently visible field of vision of the user can be calculated with the aid of known standard projection, scaling, and rotation methods from matrix-algebra. Such methods are already known under the names "ray-tracing" (beam retracing), "vector graphics" or "texture mapping" (image projection on three-dimensional grid network bodies).

The position PB and orientation B of the observer or of the spectacles is ascertained with the aid of the pocket computer in order to represent the currently acquired image section. This occurs with the inertial navigation method described above or e.g. via GPS navigation. A precise, locally referenced GPS-like navigation method can also be used, which can also determine the position PB of the observer sufficiently accurately in the range of millimeters or centimeters via radio triangulation through a measurement of time duration differences by means of a number M of reference transmissions. The exact absolute position $PRj=(XRj, YRj, ZRj)$ with ($j=1, \ldots, M$) the reference transmitter is thereby preferably stored in the pocket computer.

The spatial direction or the orientation B of the spectacles of the vision aid system according to the invention can also be determined via a gravitation based inclination sensor or other method (e.g. radio triangulation). The acquired video image of the camera in the spectacles may optionally be combined with the three-dimensional grid network model and be used e.g. for the "texture mapping". In this way, the potentially distracting background of the video image can be masked out in order to depict only the objects located in the vicinity of the user. All distracting background parts of the image may thus be depicted e.g. black, i.e. no electrical stimulation takes place at these positions in the implant. In doing so, the objects lying in the foreground of the three-dimensional grid network model deliver, with their profile, the borderlines to the sections of the video image which are to be depicted.

The generation of the three-dimensional map for the environment of the user can also be carried out by means of the electronic components, which are not integrated in the spectacles of the vision aid system. The video images acquired by the spectacles and the respectively corresponding position PB and orientation B of the spectacles can then be conveyed to the pocket computer or to a three-dimensional server or per radio or a cable connection, which can generate or update the three-dimensional map of the environment with these data. In addition, the so-called batch compensation method or other methods can, for example, be employed.

For the above-mentioned inertial navigation, acceleration sensors and electronic integrators are in principle applied, wherein the measurements of the acceleration sensors are integrated by means of the electronic integrators. An acceleration sensor normally consists of an accelerated reference mass M, which is elastically mounted in a carrier. The position of the mass relative to the carrier can be capacitively determined with comb-like measurement structures. For this purpose, the comb-like measurement structures are fixed to the carrier as well as to the reference mass. In dependence upon the distance s, around which the intermeshing comb-like measurement structures displace against each other, a change in the electrical capacity of the arrangement results and thereby a corresponding measure for the mechanically acceleration a. With known spring strength D of the mounting of the reference mass, the spring force results from the formula $F=D \cdot s$ and, by equating the known formula for the acceleration force $F=m \cdot a$, the measure for the acceleration a of the reference mass results with $a=(D/m) \cdot s$. Such silicon acceleration sensors manufactured in semi-conductor processes having small dimensions are already available in three-dimensional formats, such as e.g. the component "ADXL 330" of the company Analog Devices.

With the method of inertial navigation, it is advantageous to mount the acceleration sensor in a gyroscope rotatable about all three spatial axes in order to obtain a gyroscopic stabilisation, i.e. a selected fixed spatial orientation of the arrangement. The number of the required acceleration sensors can thus be reduced to a single three-dimensional xyz-sensor.

An electronic integrator can be constructed either analogue with the aid of precise operation amplifying circuits or can be realised with the adoption of a digital processor having diverse mathematically integration methods, which preferably adapt their precision to the input signal. Some known integration methods are, for example, the Euler method, the Runge-Kutta method, the Bulirsch-Stoer method and the Adams-Gear method. For the realization of an electronic integrator, methods can also be applied that are base upon modifications or combinations of the above-mentioned methods. A numerical integration method is, as a general rule, more precise than electrical integration methods and is therefore preferably employed with the vision aid system according to the present invention.

In the following, the present invention is more closely explained based on the preferred embodiments with reference to the accompanying drawings. They show:

BRIEF DESCRIPTION OF THE DRAWINGS

FIG. 7 a schematic representation of the vision aid system according to a further preferred embodiment of the present invention with two cameras for acquisition of a stereoscopic image;

FIG. 8 a schematic representation of the vision aid system according to a further preferred embodiment of the present invention with sensor arrays.

DETAILED DESCRIPTION

Figure 1:
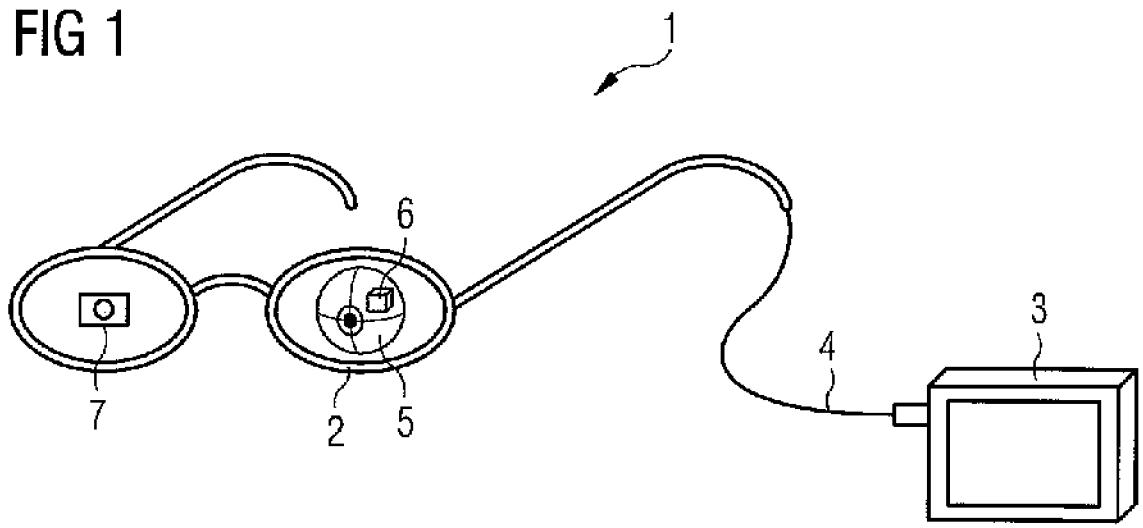
FIG. 1 a schematic representation of the vision aid system according to a preferred embodiment of the present invention with a cable connected coupling between the spectacles and the pocket computer-version.

In FIG. 1 a schematic representation of the vision aid system 1 according to a preferred embodiment of the present invention is shown. In this embodiment, the vision aid system 1 according to the invention comprises spectacles 2 which, in their shape, resemble normal spectacles and can also be worn by the user of the vision aid system 1 like normal spectacles. An electronic camera 7 which acquires video images in the field of vision of the vision aid system and transforms them into electrical image information with picture elements (pixels) is integrated in the spectacles 2. In the embodiment illustrated in FIG. 1, the entire system 1 of the vision aid according to the invention comprises spectacles 2 and a pocket computer 3 which can, for example, be carried as a separate unit on the body of the user. The spectacles 2 and the pocket computer 3 are connected with one another via a data conductor 4, which can also optionally encompass a power conductor for conveying power from the pocket computer 3 to the spectacles 2.

The vision aid system according to the invention comprises electronic means for electronic processing of the acquired image data. These electronic means are preferably accommodated in a calculating unit integrated in the vision aid system and/or in the separate unit 3, which can exchange image data and/or control data with the camera via the data conductor 4. In the embodiment illustrated in FIG. 1, electronic components are contained in the separate element or the pocket computer 3, which can electronically process the image data acquired by the camera 7 and transmitted via the data conductor 4. The image data processed by the electronic components in the pocket computer 3 can be made visible on a display (not shown) and be viewed there by the user.

In an application of the vision aid according to the invention for assisting a vision-impaired user, the image data processed by the electronic components in the pocket computer 3 may be transmitted back to the spectacles 2 via the data conductor 4 and relayed to the microelectronic stimulation device 6 implanted in the eye 5 of the user. The transfer of the image data from the spectacles 2 to the microelectronic stimulation device 6 takes place, for example, wirelessly via an inductive and/or optoelectronic interface. The microelectronic stimulation device 6 transforms the received image data into electrical stimulation impulses and delivers these to the ganglion cells of the retina and the optic nerve, whereby a corresponding image is visualized to the user.

In addition to the realistic reproduction of the image acquired by the camera 7, particular objects in the acquired image can, through additional information, be specifically accentuated and visualized to the user with the vision aid system according to the invention. The accentuation of particular objects can, for example, take place through use of different grey-scales or through use of particular colours for the visualization of the related objects. Furthermore, particularly objects in the direct vicinity of the user can be specially accentuated through the visualization of information on the distance to the related objects. In this way, for example, objects located in the near vicinity can be depicted in another colour or grey-scale than more distantly lying objects. Additionally or alternatively, more distant objects can be masked out of the acquired image. Furthermore, the environment of the user can, for example, be visualized via an outline depiction.

In an application of the vision aid according to the invention in connection with an above-described retina implant system for assistance of a vision-impaired user, a microelectronic stimulation device 6, which receives the image data acquired by the external camera 7, can be implanted in the eye 5 of the user. The micro-electronic stimulation device 6 is implanted in the region of the retina and comprises a plurality of stimulation electrodes which deliver electrical stimulation impulses to the retina corresponding to the received image data. In this way, the image acquired by the camera 7 is converted into electrical signals and delivered to the ganglion cells of the retina and the optic nerve via stimulation electrodes of the stimulation device 6 by means of electrical stimulation impulses in order to restore or to improve the visual faculty of the user.

The spectacles 2 and the separate unit or the pocket computer 3 of the vision aid system 1 are connected with one another via a cabled data conductor and/or power conductor 4 and can transfer data in both directions over this communication path. In one direction, the image data acquired by the electronic camera 7 in the spectacles can be transmitted to the pocket computer 3 and, in the other direction, the pocket computer 3 can, for example, transmit control data or stimulation data to the camera 7. These control data sent to the camera 7 from the separate component 3 serve, for example, for setting the sharpness, the direction, the focus or the zoom of the camera 7, the selection or the enlargement of a particular image section that the camera 7 should acquire.

Figure 2:
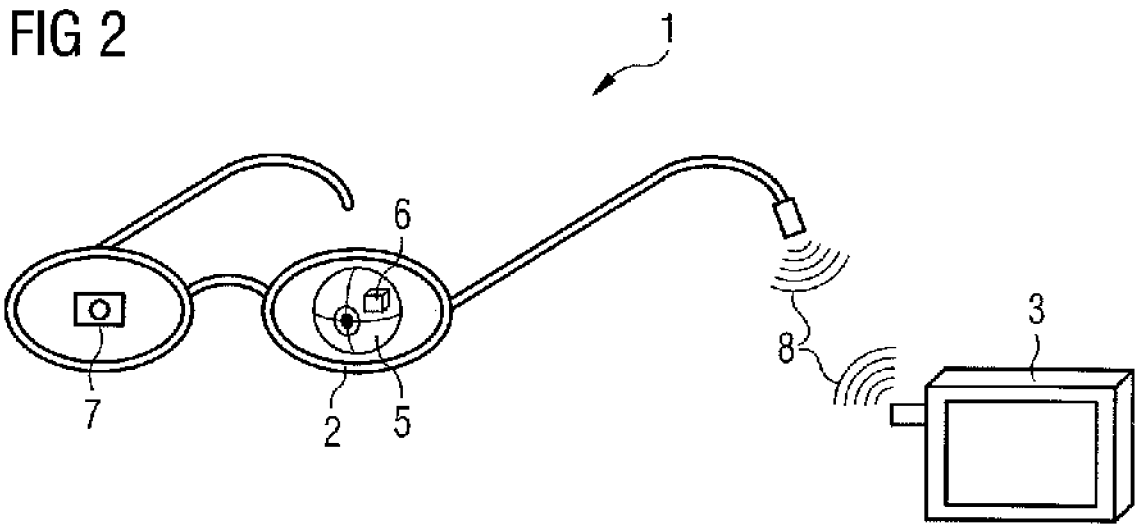
FIG. 2 a schematic representation of the vision aid system according to a further preferred embodiment of the present invention with a wireless coupling between the spectacles and the pocket computer.

FIG. 2 shows a schematic representation of the vision aid system according to a further preferred embodiment of the present invention having a wireless communication path. The configuration of the embodiment of the vision aid system according to the invention illustrated in FIG. 2 essentially corresponds to the configuration of the embodiment depicted in FIG. 1, so that reference can be made to the description of FIG. 1. As distinguished from the previously described embodiment, a wireless data conductor 8 is provided in the embodiment depicted in FIG. 1 [sic] instead of the cable conductor 4. Such a wireless data conductor 8 may, for example, be accomplished as a bi-directional radio connection between the spectacles 2 and the separate unit or the pocket computer 3 of the vision aid system 1. Via the bi-directional wireless data conductor 8, the spectacles 2 and the separate unit or the pocket computer 3 of the vision aid system 1 can communicate with one another and exchange image data or control data.

Figure 3:
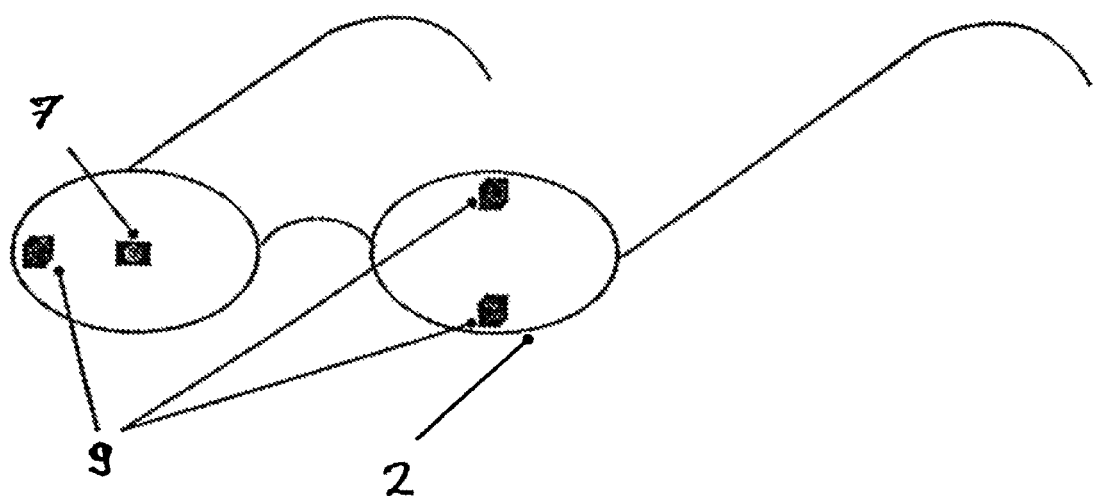
FIG. 3 a schematic representation of the vision aid system according to a further preferred embodiment of the present invention with three-dimensional or n-dimensional acceleration sensors, where $n=1, 2, 3, 4, 5, 6, \ldots$.

FIG. 3 shows a schematic representation of the vision aid system according to a further preferred embodiment of the present invention with three-dimensional acceleration sensors 9. There, both the camera 7 as well as three acceleration sensors 9 are arranged on the spectacles 2 and, in this way, are coupled with one another in the movements. The acceleration sensors 9 measure the translational acceleration $[\ddot{x}\, \ddot{y}\, \ddot{z}]$ of the camera 7 in the three spatial directions $[x, y, z]$. Additionally, the angular acceleration [$\ddot{x}$ $\ddot{y}$ $\ddot{z}$ $\ddot{\phi}_x$ $\ddot{\phi}_y$ $\ddot{\phi}_z$] of the camera 7 about the three spatial axes can be ascertained from the translational acceleration values of the sensors 9.

Figure 4:
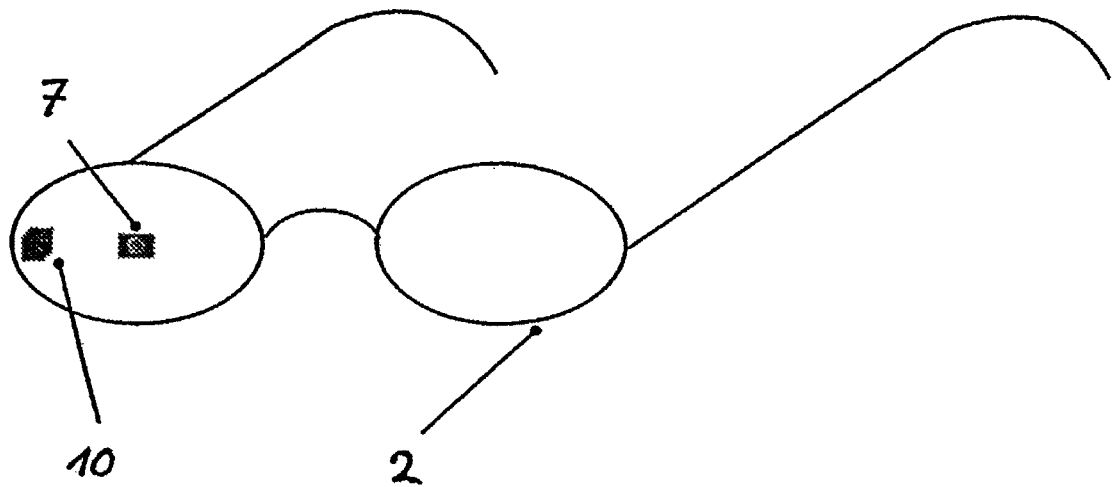
FIG. 4 a schematic representation of the vision aid system according to a further preferred embodiment of the present invention with a six-dimensional acceleration sensor.

FIG. 4 shows a schematic representation of the vision aid system according to a further preferred embodiment of the present invention with a six-dimensional acceleration sensor. The six-dimensional acceleration sensor 10 is, like the camera 7, arranged on the spectacles 2 and thereby performs the same movements and accelerations as the camera 7. This six-dimensional acceleration sensor 10 is able to measure both the translational acceleration [$\ddot{x}$ $\ddot{y}$ $\ddot{z}$] of the camera 7 as well as the angular acceleration [$\ddot{x}$ $\ddot{y}$ $\ddot{z}\ddot{\phi}_x$ $\ddot{\phi}_y$ $\ddot{\phi}_z$] of the camera about the three spatial axes.

With the measurements delivered by the acceleration sensor 9 and the angular acceleration sensor 10, a change of the spatial orientation of the camera 7 relative to a previous spatial orientation of the camera 7 can be determined. To this end, the spatial position or the orientation of the camera 7 relative to a previous position or orientation of the camera 7 is determined by means of the electronic means of the vision aid system 1 by use of an inertial navigation method.

Figure 5:
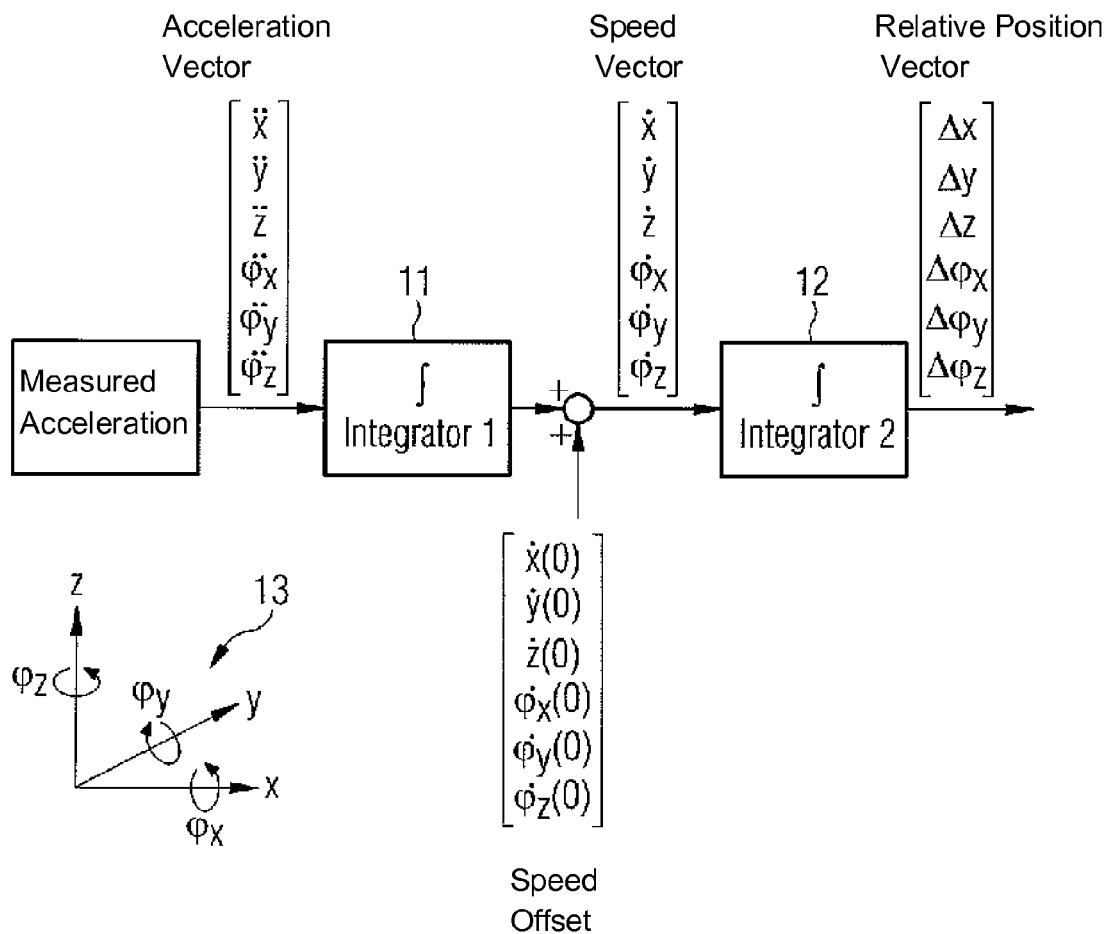
FIG. 5 a schematic representation of the calculation carried out in the vision aid system according to the invention for position determination of the vision aid system according to a preferred embodiment of the present invention.

FIG. 5 shows a schematic representation of the calculation carried out in the vision aid system according to the invention for the position determination of the vision aid system according to a preferred embodiment of the present invention. The electronic means of the vision aid system 1 according to the invention comprises electronic integrators 11 and 12, which are able to numerically execute a mathematically integration. As illustrated in FIG. 5, a six-dimensional acceleration vector is able to be generated from the orthogonal acceleration measurements measured by the acceleration sensors, which vector contains the three translational acceleration values and the three angular acceleration values. The indices x, y, z of the vector entries respectively relate to the orthogonal spatial axes of the inertial system 13 of the camera 7. The angular orientation of the camera can also be determined by evaluation of previous angular position values, by a compass, a Hall probe and/or a gravitation based inclination sensor.

The electronic components of the pocket computer 3 are constructed such that they can carry out the numerical integration of the measurements delivered by the acceleration sensors in order to determine the spatial position and orientation of the camera. For this purpose, a six-dimensional speed vector, which contains three translational speed values and three rotational speed values, is generated from the six orthogonal acceleration measurements of the acceleration vector by means of the first integrator 11. Via the change of the acquired image data and taking account of the acceleration measurements ascertained by the acceleration sensors coupled with the camera, the current speed of the camera can also consequently be determined. Here, a speed-offset can be taken into account by a simple vector addition of a six-dimensional speed-offset vector and in this way be cancelled from the calculations. Input means can also be provided, through which the measurement of the acceleration sensors and/or the angular acceleration sensors is set to zero.

By means of the second integrator 12, a six-dimensional relative position vector is generated from the speed vector, which specifies the deviation of a previous position of the camera to a subsequent camera position. This six-dimensional relative position vector contains three location differential coordinates ($\Delta x$, $\Delta y$, $\Delta z$), which specify the deviation of the location coordinates (x, y, z) of the previous camera position to the following camera position, and three angular differential coordinates ($\Delta\phi x$, $\Delta\phi y$, $\Delta\phi z$), which specify the deviation of the angular position ($\phi x$, $\phi y$, $\phi z$) of the previous camera position to the subsequent camera position. The integration may take place in discrete time increments or may also be carried out continuously, whereby the time integration increments in the integration of the acceleration measurements should be smaller than the time period within which the acceleration of the camera changes substantially.

Figure 6:
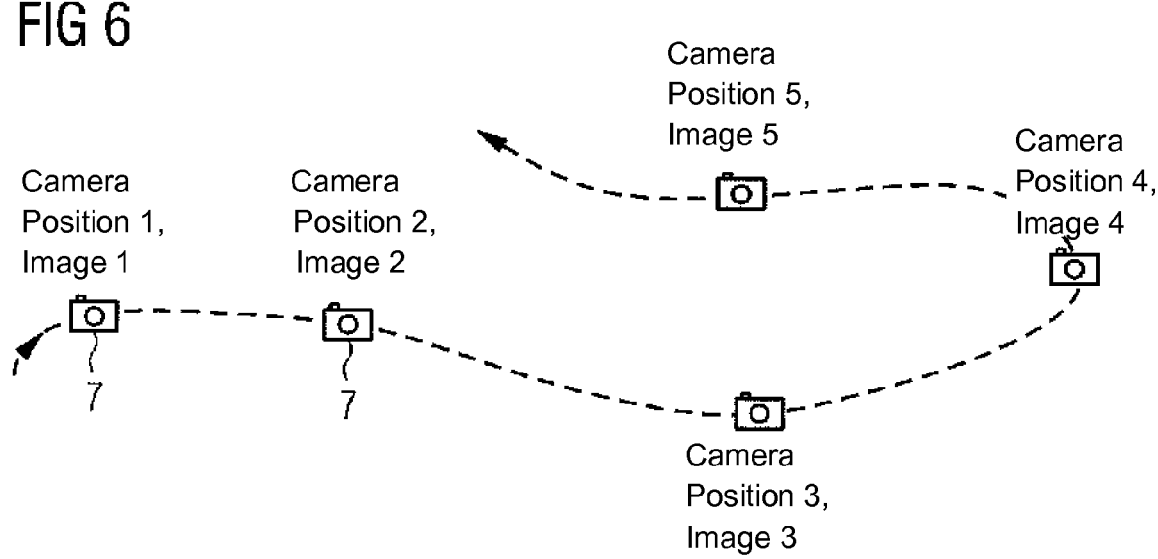
FIG. 6 a schematic representation of a movement trace with a number of different successive positions of the vision aid system according to the present invention.

FIG. 6 shows a schematic representation of a movement trace with a number of different successive positions of the vision aid system according to the present invention. With the vision aid system according to the invention, a sequence of at least two images can be acquired to the camera in respectively different positions of the camera or a sequence of images in fixed time intervals at respectively different position of the camera can be recorded. From such a sequence of images acquired in relatively short time secession after one another with different camera positions, a stereoscopic reproduction of the acquired images, i.e. a three-dimensional reproduction of the acquired environment, can be calculated and visualized by means of the electronic means.

In addition, from the sequence of the acquired images from different camera positions, the spatial position and/or orientation of the camera 7 is calculated by means of the electronic means. By use of location differential coordinates and angular differential coordinates, the relative position of the camera 7 in reference to the camera position or the position of the user of the vision aid system at the acquisition of the previous or successive image can be assigned to each acquired image of the sequence. In doing so, older images of a sequence of acquired images can be weighted increasingly weakly in their influence on the calculations or may have no further influence on the calculations. In this way, a three-dimensional reproduction of the acquired images and the objects located therein can be calculated and visualized with the vision aid system according to the invention with only one camera 7 based on a sequence of serially acquired images from different camera positions.

FIG. 7 shows a schematic representation of the vision aid system according to a further preferred embodiment of the present invention having two cameras 7. The second camera is integrated in the spectacles at a position spaced from the first camera. With the aid of both cameras 7, two images can be simultaneously acquired and, by means thereof, a stereoscopic image generated. With the acquired stereo images, a three-dimensional reproduction of the acquired image and the objects located therein can be calculated by means of the electronic means of the vision aid system and visualized to the user. The calculation of the three-dimensional reproduction of the acquired image can be carried out by application of the batch compensation method.

FIG. 8 shows a schematic representation of the vision aid system according to a further preferred embodiment of the present invention with sensor arrays. In this embodiment, multiple distance sensors, which are arranged in a shape of a one-dimensional or multi-dimensional array 14, are provided on the spectacles 2. The sensors may thereby serve to determine the distance of objects and/or obstacles in the acquired image and to make this available to the vision aid system as additional information. The distance sensors may be constructed as ultrasound sensors or rotating laser scanners in the visible or invisible wavelength range. Other types of sensors or actuators can also be provided in the spectacles 2, such as e.g. ultrasound sensors, infrared sensors, photo-sensors, lasers or combinations thereof.

Figure 9:
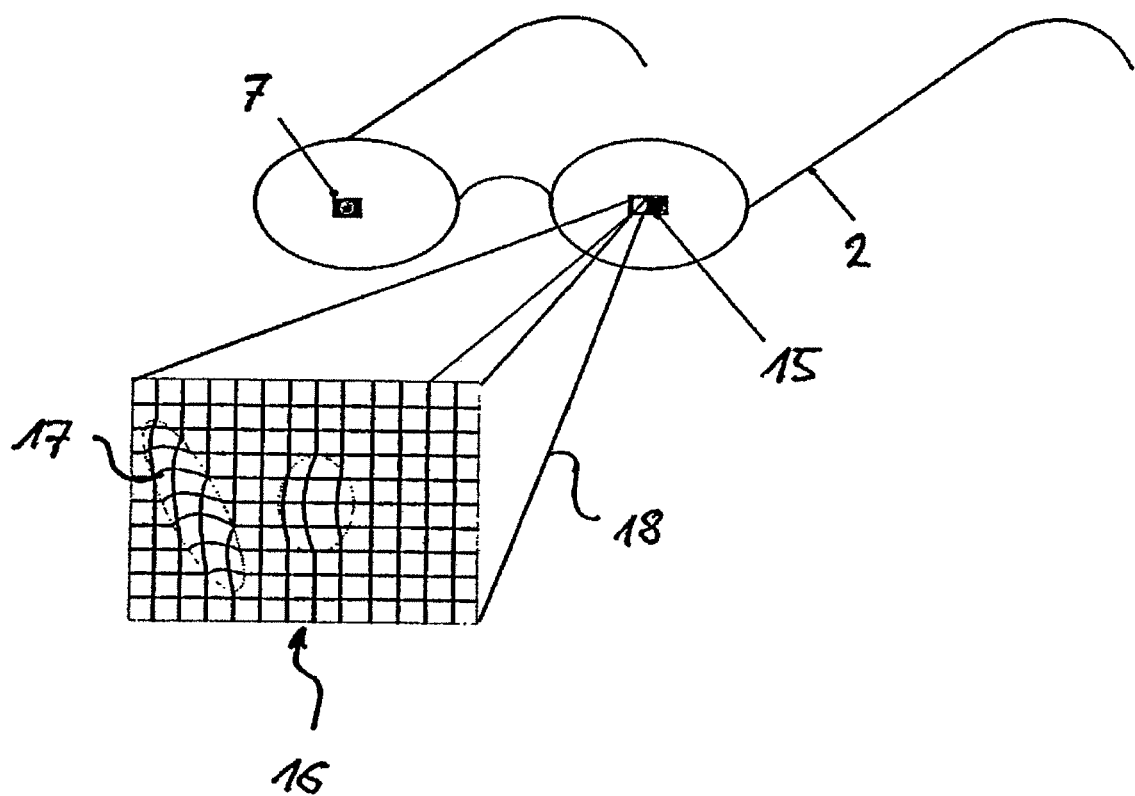
FIG. 9 a schematic representation of the vision aid system according to a further preferred embodiment of the present invention with a grid projector.

FIG. 9 shows a schematic representation of a further preferred embodiment of the vision aid system according to the invention. In this preferred embodiment, the vision aid system is equipped with a light source 15 in order to illuminate the image area to be acquired by the camera with light 18 in the visible or invisible wavelength range, with infrared light, or with infrared or visible laser light 18, while the camera 7 of the vision aid system is sensitive to the corresponding wavelength range. By means of such a light source 15, the image area to be acquired by the camera can be illuminated with a homogeneous or structured stripe pattern. For projection of a structured stripe pattern 16 onto the image area to be acquired by the camera 7, a laser projector with a suitable deflection unit may also be used, a grid projector or a projection mask which is positioned in the beam path of a light source. Interference effects can also be generated with laser light and projected onto the image area to be acquired by the camera.

FIG. 9 shows a schematic representation of a vision aid system, which is equipped with a grid projector. The grid projector exposes the image area to be acquired by the camera with a stripe or grid pattern, which falls on the objects in the image area and is reflected there-from. Distortions of the stripe or grid pattern thereby result, from which conclusions on the position, size and situation of the objects in the acquired image can be drawn. With the aid of the electronic means of the vision aid system 1, a three-dimensional reproduction of the acquired image and the objects located therein can be generated and visualized from the distortions, deflections, displacements or other changes of the stripe or grid pattern.

The vision aid system can record alternately an image of the image area to be acquired under illumination with a stripe pattern 16 and an image of the image area to be acquired without stripe pattern 16, and combine or compare the image data of the acquired images with one another by means of the electronic means. The image area to be acquired may be scanned by means of a column- and line-by-line controlled laser beam 18 in order to obtain additional image data and/or information about the distance of objects in the acquired image. At the same time, the vision aid system 1 according to the invention may be equipped with a photo-detector, which determines the spatial position of objects in the acquired image and/or their distance to the camera, in that the photo-detector carries out a time duration measurement of the laser light 18 reflected by a related picture element.

LIST OF THE REFERENCE CHARACTERS

1 vision aid system
2 spectacles
3 separate electronic unit or pocket computer
4 cable connected data conductor and/or power conductor between 2 and 3
5 eye of the user
6 implantable stimulation device
7 camera
8 wireless data conductor between 2 and 3
9 sensors for measurement of the translational or angular acceleration
10 sensor for measurement of the translational and angular acceleration
11 electronic means or electronic integrator I
12 electronic means or electronic integrator II
13 inertial system of the camera
14 array of sensors
15 light source or grid projector
16 projected grid or stripe pattern
17 distortion in the reflected grid or stripe pattern
18 light beams or laser-light beams

The invention claimed is:

1. A vision aid system comprising:
at least one first camera for acquisition of an image having a plurality of image data;
electronic means for processing the acquired image data; and
a stimulation device implantable in a body at a vision organ for reproduction of the processed image through corresponding stimulation of the vision organ,
wherein additional information and/or particular attributes regarding the spatial position of objects in the acquired image is visualized in the reproduction of the processed image, which information is associated with objects in the acquired image,
wherein a change of the position [$\Delta x\ \Delta y\ \Delta z\ \Delta\phi_x\ \Delta\phi_y\ \Delta\phi_z$] of the camera relative to a previous position of the camera is determined by means of the electronic means through double integration of acceleration measurements delivered by a number of acceleration sensors and used in determining the spatial position of the objects, and
wherein the time integration increment in the integration of the acceleration measurements is smaller than the time span within which the acceleration of the camera changes significantly.

2. The vision aid system of claim 1,
wherein, by means of the electronic means, a relative position vector is determined from the acceleration measurements delivered by a number of acceleration sensors, which vector contains location differential coordinates ($\Delta x$, $\Delta y$, $\Delta z$) that specify the deviation of the location coordinates (x, y, z) of a previous camera position to the subsequent camera position, and contains three angular differential coordinates ($\Delta\phi_x$, $\Delta\phi_y$, $\Delta\phi_z$) that specify the deviation of the angular position ($\phi_x$, $\phi_y$, $\phi_z$) of the previous camera orientation to the subsequent camera orientation.

3. The vision aid system of claim 1,
wherein, for integration of the acceleration measurements, a numerical integration method, the Euler method, the Runge-Kutta method, the Bulirsch-Stoer method, the Adams-Gear method, or combinations of these methods are applied.

4. The vision aid system of claim 1, wherein a second camera is provided, which together with the first camera acquires stereo images,
wherein, by means of the electronic means with the acquired stereo images, a three-dimensional reproduction of the acquired image and the objects located therein is calculated and visualized, and
wherein the electronic means carry out the calculation of the three-dimensional reproduction of the acquired image by use of the batch compensation method.

5. The vision aid system of claim 1, wherein input means are provided, through which the measurement of acceleration sensors and/or angular acceleration sensors can be set to zero.

6. The vision aid system of claim 1,
wherein an angular orientation of the camera is determined by evaluation of previous angular position values, by a compass, a Hall-probe and/or a gravitation-based inclination sensor.

7. The vision aid system of claim 1, wherein the vision aid system alternately acquires an image of the image area to be acquired under illumination with a stripe pattern and an image of the image area to be acquired without illumination, and combines or compares the image data of the acquired images with one another by means of the electronic means.

* * * * *